(12) United States Patent
Polonka et al.

(10) Patent No.: US 7,892,524 B2
(45) Date of Patent: *Feb. 22, 2011

(54) SUNSCREEN COMPOSITE PARTICLES

(75) Inventors: Jack Polonka, Peekskill, NY (US);
Gabriela Maria Wis, Cos Cob, CT (US); John Brian Bartolone, Bridgeport, CT (US); Lawrence Alan Wilen, New Haven, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/330,740

(22) Filed: Dec. 9, 2008

(65) Prior Publication Data

US 2009/0324659 A1 Dec. 31, 2009

Related U.S. Application Data

(63) Continuation-in-part of application No. 12/164,136, filed on Jun. 30, 2008.

(51) Int. Cl.
*A61K 8/00* (2006.01)
*A61K 8/18* (2006.01)
*A61K 8/02* (2006.01)
*A61K 8/73* (2006.01)

(52) U.S. Cl. .................. 424/59; 424/63; 424/401; 424/70.13

(58) Field of Classification Search ............ 424/59
See application file for complete search history.

(56) References Cited

U.S. PATENT DOCUMENTS

| | | |
|---|---|---|
| 3,895,104 A | 7/1975 | Karg |
| 4,731,242 A | 3/1988 | Palinczar |
| 5,264,207 A | 11/1993 | Bommelaer et al. |
| 5,733,531 A | 3/1998 | Mitchnick et al. |
| 5,783,657 A | 7/1998 | Pavlin et al. |
| 5,972,359 A | 10/1999 | Sine et al. |
| 5,997,890 A | 12/1999 | Sine et al. |
| 5,998,570 A | 12/1999 | Pavlin et al. |
| 6,036,945 A | 3/2000 | Deblasi et al. |
| 6,174,533 B1 | 1/2001 | SaNogueira, Jr. et al. |
| 6,242,509 B1 | 6/2001 | Berger et al. |
| 6,280,710 B1 | 8/2001 | Deblasi et al. |
| 6,399,713 B1 | 6/2002 | MacQueen et al. |
| 6,402,408 B1 | 6/2002 | Ferrari |
| 6,485,713 B1 | 11/2002 | Bonda et al. |
| 6,492,458 B1 | 12/2002 | Pavlin |
| 6,552,160 B2 | 4/2003 | Pavlin |
| 6,685,966 B1 | 2/2004 | Dominique et al. |
| 6,835,399 B2 | 12/2004 | Collin |
| 6,870,011 B2 | 3/2005 | MacQueen et al. |
| 6,875,245 B2 | 4/2005 | Pavlin |
| 7,056,642 B2* | 6/2006 | Kano et al. .............. 430/271.1 |
| 7,253,249 B2 | 8/2007 | Pavlin |
| 7,264,795 B2 | 9/2007 | Pflucker et al. |
| 7,329,719 B2 | 2/2008 | Pavlin |
| 7,351,418 B2 | 4/2008 | Collin |
| 2004/0126336 A1* | 7/2004 | Hansenne et al. ............. 424/59 |
| 2005/0163730 A1 | 7/2005 | Rosevear et al. |
| 2005/0163813 A1 | 7/2005 | Kosbach et al. |
| 2005/0197479 A1 | 9/2005 | Pavlin |
| 2005/0249684 A1 | 11/2005 | Dobkowski et al. |
| 2005/0276833 A1 | 12/2005 | Fowler |
| 2006/0099168 A1 | 5/2006 | Corzani et al. |
| 2006/0177393 A1* | 8/2006 | Candau ....................... 424/59 |
| 2006/0280763 A1 | 12/2006 | Yoshida et al. |
| 2007/0099886 A1* | 5/2007 | Gupta ........................ 514/184 |
| 2007/0212315 A1 | 9/2007 | Pastor et al. |
| 2008/0115846 A1 | 5/2008 | Josso et al. |
| 2009/0016971 A1 | 1/2009 | Gaudry et al. |

FOREIGN PATENT DOCUMENTS

| | | |
|---|---|---|
| EP | 0 904 768 A1 | 9/1998 |
| EP | 1 388 550 A1 | 8/2003 |
| EP | 1 475 078 A1 | 5/2004 |
| EP | 1 642 924 A1 | 9/2005 |
| EP | 1 813 266 A1 | 12/2006 |
| EP | 2 005 940 A2 | 6/2008 |
| GB | 2 166 107 A | 4/1986 |
| WO | 01/87847 A2 | 11/2001 |
| WO | 2009/007264 A2 | 1/2009 |

OTHER PUBLICATIONS

Krishnan et al. (Fluorescence of Sunscreens Adsorbed to Dielectric Nanospheres: Parallels to Optical Behavior on HaCat Cells and Skin, Photochemistry and Photobiology, 2006,82: 1557-1565.*
Co-Pending Application: Polonka et al.; Entitled: Sunscreen Composite Particles In Cosmetic Compositions.
Co-Pending Application: Polonka et al.; Entitled: Sunscreen Composite Particles Dispersed In Water-In-Oil Cosmetic Compositions.
Co-Pending Application: Polonka et al.; Entitled: Sunscreen Composite Particles And Porous Particles In Cosmetic Compositions.
PCT International Search Report PCT/EP2009/057150; International Filing Date Jun. 10, 2009.

* cited by examiner

*Primary Examiner*—Sreeni Padmanabhan
*Assistant Examiner*—Timothy E Betton
(74) *Attorney, Agent, or Firm*—Milton L. Honig

(57) ABSTRACT

Composite particles for providing UV photo protection in cosmetic compositions are reported which include an organic sunscreen agent dispersed within a condensation polymerized resin having carboxylic acid groups and a dielectric constant ranging from 6.5 to 18.

11 Claims, No Drawings

SUNSCREEN COMPOSITE PARTICLES

CROSS REFERENCES

This application claims benefit from Ser. No. 12/164,136 filed Jun. 30, 2008.

BACKGROUND OF THE INVENTION

1. Field of the Invention

The invention concerns sunscreen composite particles for use in cosmetic compositions to deliver protection against ultraviolet radiation.

2. The Related Art

Ultraviolet radiation can be damaging to skin. Immediate damage may be in the form of erythema. More long term is the concern of initiating cancerous growth. For these reasons, photoprotective agents known as sunscreens have been incorporated into cosmetic products.

Organic sunscreen agents have a number of disadvantages. Under the influence of ultraviolet radiation, the sunscreen agents themselves are known to degrade. Photostability may only be a matter of hours. Consumers thinking that they are fully protected with their sunscreen application, often expose themselves for a time beyond the photostability limit. Further, organic sunscreen agents can under certain circumstances cause skin irritation. A still further problem is that some sunscreen agents may not be fully compatible with other sunscreen or formulation components.

Attempts have been made to address the aforementioned problems. One approach has been to encapsulate the sunscreen agent. A few encapsulates are commercially available.

A first commercial material is known as Sun Caps 664® sold by Particle Sciences, Inc. of Bethlehem, Pa. Sun Caps 664® is formulated with a concentration of octylmethoxycinnamate (OMC) of 21.5% encapsulated in a binder that includes beeswax, carnauba wax, Vinyl Pyrrolidone/Eicosene Copolymer and emulsifiers (PEG-100 stearate, PEG-20, bis-PEG-12 dimethicone, sorbitan tristearate and Steareth-100). Sun Caps® are formed in a process revealed in U.S. Pat. No. 5,733,531. The encapsulates are supplied as an aqueous dispersion containing up to 65% solids.

Another hydrophilic composite particulate commercially available is sold by Rona Division of EMD Chemicals under the trademark Eusolex® UV Pearls® OMC. UV Pearls® OMC is prepared and described in U.S. Pat. No. 7,264,795. This material is delivered as 40% particles in 60% aqueous carrier. The particles are structured with a core of greater than 70% octylmethoxycinnamate surrounded by a coating of about 10% silica, about 1-2% polyvinylpyrrolidone (as binder), and minor ingredients.

While the known encapsulates have shown some advantages, much improvement remains to be done with respect to enhanced activity and photostability. The present invention has sought to address these issues.

SUMMARY OF THE INVENTION

Composite particles are provided which include an organic sunscreen agent dispersed within a condensation polymerized resin, the composite particles having a number average particle size ranging from about 10 to about 2,000 nm, the condensation polymerized resin having carboxylic acid groups, and wherein the composite particles have a dielectric constant ranging from 6.5 to 18.

DETAILED DESCRIPTION OF THE INVENTION

Now it has been found that improved UV photo protection can be achieved by a cosmetic composition that incorporates composite particles of an organic sunscreen agent surrounded by a specified type of condensation polymerized resin. The condensation polymerized resin will bear carboxylic acid groups within its structure. Most important, the composite particles require a dielectric constant ranging from 6.5 to 18.

Relative weight ratio of organic sunscreen agent to condensation polymerized resin may range from about 5:1 to about 1:10, preferably from about 1.5:1 to about 1:8, more preferably from about 1:1 to about 1:6, optimally from about 1:1 to about 1:3. Amounts of the condensation polymerized resin may range from about 10% to about 99.5% by weight of the composite particles. More preferably the weight of the condensation polymerized resin may range from about 30% to about 98%, optimally from about 50 to about 85% by weight of the composite particles. Amounts of the sunscreen agent may range from about 0.5 to about 90%, preferably from about 2 to about 70%, optimally from about 30 to about 50% by weight of the composite particles.

Amounts of the composite particles when placed within a cosmetic emulsion composition may range from about 0.1 to about 30%, preferably from about 2 to about 15%, optimally from about 4 to about 10% by weight of the cosmetic composition.

Number average particle size of the composite particles may range from about 10 to about 2,000 nm, preferably from about 40 to about 1,200 nm, and optimally from about 50 to about 1000 nm.

Composite particles of the present invention are formed between an organic sunscreen agent and a condensation polymerized resin. The resin may be a polyester or polyamide. Most preferably chosen is a polyamide. Ester-terminated polyamides are most useful. Two examples are polyalkyleneoxypolyamide (PAOPA) and ester-terminated poly(esteramide) (ETPEA) resins.

The polyalkyleneoxypolyamide resins that may be useful herein are outlined in U.S. Pat. No. 6,492,458 B1 herein incorporated by reference. These PAOPA materials may be prepared by combining reactants comprising a monocarboxylic acid compound, a diamine compound, and a dibasic acid. Specifics of these reactants are described hereinbelow. Commercially the resins are available from the Arizona Chemical Company under the trademark Sylvaclear® PA 1200V, designated by INCI nomenclature as Polyamide-3, and as Sylvaclear® AF1900V. Exemplary monocarboxylic acids of the formula $R^1$—COOH include, without limitation, stearic acid ($C_{18}$), 1-eicosanoic acid ($C_{20}$), 1-docasanoic acid ($C_{22}$, also known as behenic acid), dotricontanoic acid ($C_{32}$), tetratriacontanoic acid ($C_{34}$), pentatriacontanoic acid ($C_{35}$), tetracontanoic acid ($C_{40}$), tetraacontanioc acid ($C_{44}$), dopentaacontanoic acid ($C_{54}$), tetrahexaacontanoic acid ($C_{64}$), and dohexaacontanoic acid ($C_{72}$). These monocarboxylic acids are available from many commercial suppliers, including Aldrich Chemical (Milwaukee, Wis.; www.sigma-aldrich.com).

Another suitable monocarboxylic acid is the oxidized (specifically, carboxyl terminated) polyethylene materials sold by Baker-Petrolite (Sugar Land, Tex.; www.bakerhughes.com/bapt/; division of Baker Hughes; www.bakerhughes.com) as their UNICID™ acids. UNICID™ acids are fully saturated, linear carboxylic acids with average carbon chain lengths ranging from C24 to C50. Acid values for UNICID™ acids vary from 60 to 115.

Still other suitable monocarboxylic acids are the alpha-branched carboxylic acids prepared by oxidizing higher molecular weight Guerbet alcohols. Such products are available from Jarchem Industries Inc. (Newark, N.J.; www.jarchem.com) as their JARIC™ acids. JARIC™ I-36 acid is a suitable monocarboxylic acid for the resins of this invention.

The diamine reactant has two amine groups, both of which are preferably primary amines, and is represented by the formula $HN(R^{2a})$—$R^2$—$N(R^{2a})H$. $R^{2a}$ is preferably hydrogen, but may also be an alkyl group or may also join together with $R^2$ or another $R^{2a}$ to form a heterocyclic structure. A preferred diamine is ethylene diamine, i.e., a diamine wherein $R^{2a}$ is hydrogen and $R^2$ is —$CH_2CH_2$—.

Diamines other than ethylene diamine may be referred to herein as co-diamines. When present, co-diamines are preferably used in a minor amount compared to the ethylene diamine.

Exemplary co-diamines include 1,2-diaminopropane, 1,3-diaminopropane, 1,4-diaminobutane, 1,2-diamino-2-methylpropane, 1,3-diaminopentane, 1,5-diaminopentane, 2,3-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexandeiamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,3; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminoaphthalene (all isomers, including 1,5; 1,8; and 2,3) and 4-amino-2,2,6,6-tetramethylpiperidine.

Suitable aromatic co-diamines (by which is meant molecules having two reactive, preferably primary amine groups (—$NH_2$) and at least one aromatic ring ("Ar") include xylene diamine and naphthalene diamine (all isomers).

Exemplary polyalkylene oxide-based co-diamines include without limitation, the JEFFAMINE™ diamines, i.e., poly(alkyleneoxy)diamines from Huntsman Chemical (Salt Lake City, Utah), also known as polyether diamines. Preferred polyalkylene oxide-containing co-diamines are the JEFFAMINE® ED, XTJ and D series diamines.

In certain embodiments, the polyamide resins of the invention are prepared from co-diamine, where the co-diamine is selected from 1,6-hexanediamine, xylenediamine, 1,2-propanediamine, 2-methylpentamethylenediamine, and 1,12-dodecanediamine. Suitable diamines of the present invention are available from a number of commercial sources including Aldrich (Milwaukee, Wis.); EM Industries, Inc. (Hawthorne, N.Y); Lancaster Synthesis, Inc. (Windham, N.H.) and Spectrum Quality Product, Inc. (New Brunswisk, N.J).

The dibasic acid is an organic molecule containing two carboxylic acid groups or reactive equivalent thereof. A preferred dibasic acid is polymerized fatty acid, and in particular the dimer acid component of polymerized fatty acid. Polymerized fatty acid is typically a mixture of structures, including dimer acid and trimer acid, where individual dimer acids may be saturated, unsaturatred, cyclic, acyclic, and combinations thereof. Polymerized fatty acid is typically formed by heating long-chain unsaturated fatty acids, e.g., $C_{18}$ monocarboxylic acids, to about 200-250° C. in the presence of a clay catalyst in order that the fatty acids polymerize. The product typically comprises dimer acid, i.e. $C_{36}$ dicarboxylic acid formed by dimerization of the fatty acid, and trimer acid, i.e., $C_{54}$ tricarboxylic acid formed by trimerization of the fatty acid. A more detailed discussion of fatty acid polymerization may be found in U.S. Pat. No. 3,157,681.

Because fatty acid polymerization typically forms much more dimer acid than trimer acid, those skilled in the art may often refer to polymerized fatty acid as dimer acid, even though some trimer acid, and even higher polymerization products, may be present with the dimer acid. It is preferred that the polymerized fatty acid contain less than about 20 weight percent of trimer acid, based on the total weight of the polymerized fatty acid, and that the dimer acid constitute at least about 80 weight percent of the polymerized fatty acid. More preferably, the dimer acid constitutes essentially all of the polymerized fatty acid.

Typical unsaturated fatty acids used to form polymerized fatty acid include oleic acid, linoleic acid and linolenic acid. Tall oil fatty acid, which is a mixture containing long-chain unsaturated fatty acids obtained as a byproduct of the wood pulping process, is preferred for preparing polymerized fatty acid.

Polymerized fatty acid may be hydrogenated prior to being used in the resin-forming reaction. Hydrogenation tends to provide for a slightly higher melting point and greater oxidative and color stability.

Polymerized fatty acid, dimer acid, and hydrogenated versions thereof may be obtained from a number of commercial suppliers. For example, Arizona Chemical (Jacksonville, Fla.) sells polymerized fatty acid under their UNDYME® trademark.

In addition to polymerized fatty acid, or reactive equivalents thereof, the dibasic acid may comprise a co-diacid. An exemplary co-diacid is a so-called "linear" diacid of the formula HOOC—$R^1$—COOH wherein $R^1$ is a linear $C_{4-17}$ hydrocarbon group, and more preferably is a linear $C_{6-8}$ hydrocarbon group. Linear co-diacids suitable for the present invention include 1,6-hexanedioic acid (adipic acid), 1,7-heptanedioic acid (pimelic acid), 1-8-octanedioic acid (suberic acid), 1,9-nonanedioic acid (azelaic acid), 1,10-decanedioic acid (sebacic acid), 1,11-undecanedioic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{2'}$ diacid is commercially available from Westvaco Corporation, Chemical Division, Charleston Heights, S.C. as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR) and at least one aromatic ring ("Ar"). Phthalic acids, e.g., isophthalic acid and terephthalic acid, are exemplary aromatic diacids.

In one aspect, the resin is prepared with co-diacid and the co-diacid is selected from 1,4-cyclohexane dicarboxylic acid, isophthalic acid, adipic acid, azelaic acid, sebacic acid, and dodecandioic acid.

A second class of polyamides useful for this invention are the ester-terminated poly(ester-amide) resins. These are prepared by reacting components comprising dibasic acid, diamine, polyol and monoalcohol, wherein at least 50 equivalent percent of the dibasic acid comprises polymerized fatty acid; and at least 50 equivalent percent of the diamine comprises ethylene diamine. Typical dibasic acids, and diamines have already been described hereinabove.

A further constituent of the ester-terminated poly(ester-amide) resins are the monoalcohol reactants. The monoalcohol may be represented by the formula $R^3$—OH, wherein $R^3$ is preferably a hydrocarbon group having at least ten carbon atoms. Thus, the monoalcohol can also be described as a monohydric alcohol. In one aspect, $R^3$ is a $C_{10\text{-}30}$- hydrocarbon, preferably a $C_{12\text{-}24}$ hydrocarbon, still more preferably is a $C_{16\text{-}22}$ hydrocarbon, and yet still more preferably is a $C_{18}$ hydrocarbon. Preferably, $R^3$ is linear, with the hydroxyl group located on a terminal carbon atoms, i.e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing polyamide resins of the invention.

Another suitable monoalcohol reactant is a so-called Guerbet alcohol. Guerbet alcohols have the general formula H—C(Ra)(Rb)—CH$_2$—OH wherein Ra and Rb may be the same or different and preferably represent a $C_{6\text{-}12}$ hydrocarbon group.

Another suitable monoalcohol reactant is a linear wax alcohol. Suitable linear wax alcohols are commercially available from, e.g., Petrolite Corporation (Tulsa, Okla.) under their UNILIN® trademark. These wax alcohols are typically a blend of linear alcohols having at least about 20 carbon atoms, and more typically at least about 24 carbon atoms.

A final ingredient necessary in preparing an ETPEA resin of the present invention is polyol, which may also be referred to as polyhydric alcohol. The polyol is of the formula $R^4(OH)_n$ wherein $R^4$ is an n-valent organic group. For instance, $R^4$ may be a $C_2$-$C_{20}$ organic group without hydroxyl substitution. As another example, $R^4$ may be a hydrocarbon. Typically, n is selected from 2, 3, 4, 5 and 6. Suitable polyols for use in preparing an ETPEA resin of the present invention include ethylene glycol, propylene glycol, butylene glycol, glycerol, trimethylolpropane, pentaerythritol, neopentyl glycol, tris(hydroxylmethyl)methanol, di-pentaerythritol, and tri-pentaerthyritol.

Preparation and description of the ETPEA resins are found in U.S. Pat. No. 7,329,719 B2 herein incorporated by reference.

Sunscreen agents can either be dispersed throughout the resin or can be formed as a core surrounded by resin. Dispersal throughout the resin is preferred.

Sunscreen agents according to this invention will have at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyidisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4, 4'-dimethoxybenzophenone, Octabenzone; 4-lsopropyidibenzoylmethane; Butylmethoxydibenzoylmethane; Etocrylene; and 4-isopropyl-dibenzoylmethane).

Particularly useful sunscreen agents are: 2-ethylhexyl p-methoxycinnamate, 4,4'-t-butyl methoxydibenzoylmethane, 2-hydroxy-4-methoxybenzophenone (known also as Benzophenone-3), octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, 4-methylbenzylidene camphor, bis-ethylhexyloxyphenol methoxyphenol triazine, methylene bis-benzotriazolyl tetramethylbutylphenol, dimethicodiethylbenzal malonate, isoamyl methoxycinnamate, octyl triazone, terephthalidene dicamphor sulfonic acid and mixtures thereof.

Condensation polymerized resins of the present invention will contain carboxylic acid groups and may be characterized by an acid number ranging from 3 to 15, preferably from 5 to 14, and optimally from 8 to 13. The dielectric constant required for the composite particles will range from 6.5 to 18, preferably from 7 to 15, optimally from 8 to 12. Dielectric constant is measured according to the procedure of ASTM D ISO/IEC 60250.

Composite particles of this invention may be formulated into cosmetic compositions such as creams and lotions. These will feature cosmetically acceptable carriers.

The carrier may be a liquid or solid material. Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include silicones, polyhydric alcohols, fatty alcohols, hydrocarbons, triglycerides and thickening powders.

Concentrations of the fluid silicone may range from about 5% to about 60%, more preferably from about 5% to about 40%, by weight of the composition. These silicone fluids may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and diglycerides may also be useful. Illustrative of these categories are glyceryl monostearate and glyceryl distearate.

The carriers can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytriotol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyldimethyl Taurate (e.g. Simulgel® NS and INS 100), Acrylate/Sodium Acryloyidimethyl Taurate (e.g. Simulgel® EG), Sodium Acryloyldimethyl Taurate (e.g. Simulgel® 800) and Ammonium Acryloyidimethyl Taurate/Vinyl Pyrrolidone (e.g. Aristoflex® AVC).

c. Polyacrylamide Polymers

The compositions of the present invention can optionally comprise vinyl polymerized polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

The compositions of the present invention may contain one or more other particulate materials. Nonlimiting examples of other particulate materials include colored and uncolored pigments, interference pigments, inorganic powders, organic powders, composite powders, optical brightener particles, and combinations thereof. Particulate materials may be present from about 0.01% to about 20%, more preferably from about 0.05% to about 10%, still more preferably from about 0.1% to about 5%, by weight of the composition.

Other particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, barium sulfate, calcium carbonate, cellulose acetate, PTFE, polymethyl methacrylate, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

Cosmetic compositions formulated with composite particles of the present invention may contain a variety of optional components to enhance physical properties and performance.

The optional components, when incorporated into the cosmetic compositions, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives, colorants, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents, thickeners, and vitamins and derivatives thereof.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts. Preferred anti-oxidants/radical scavengers are selected from esters of tocopherol, more preferably tocopherol acetate.

The cosmetic compositions may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The cosmetic compositions include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A typical process to manufacture composite particles of the present invention is herein described. Water in the amount of 750 gm is charged to a vessel fitted with an Escolabor™ mixer (1 liter model manufactured in Riehn, Switzerland) which has scrape surface blades (scraper). The water is then heated to 60° C. A metal beaker is charged with 125 gm Sylvaclear PA1200V® and 125 gm Parsol MCX® (2-ethylhexyl-p-methoxy cinnamate referred to as "OMC"). The beaker is placed in a water bath. The resin mixture is heated up to about 85-90° C. and mixed until homogenous. The resin from the beaker is then added slowly to the vessel of heated water with slow mixing (20% power use on the scraper) followed by a cooling period. Upon reaching 36° C., a preservative mixture is added which includes 2.5 gm Glydant Plus®, 4 gm phenoxyethanol, 2 gm methyl paraben and 2 gm propyl paraben. The combination is then mixed and cooled. Composite particles of resin/sunscreen/preservative are then separated (via centrifuge) as particulates from the water phase. The particulates were found to have a pH of 5.4 and a dielectric constant of 8.56.

EXAMPLE 2

A series of comparative experiments were conducted to demonstrate aspects of the present invention. These experiments are based upon testing of the formulas outlined under Table I.

TABLE I

| Component | Formula (Weight %) | | | | | | | |
|---|---|---|---|---|---|---|---|---|
| | 1 | 2 | 3 | 4 | 5 | 6 | 7 | 8 |
| Water Phase | | | | | | | | |
| Polysorbate 40 | 1.62 | 1.62 | 1.62 | 1.62 | 1.62 | 1.62 | 1.62 | 1.62 |
| Cetyl Alcohol | 1.55 | 1.55 | 1.55 | 1.55 | 1.55 | 1.55 | 1.55 | 1.55 |
| Glycerin Monostearate | 0.78 | 0.78 | 0.78 | 0.78 | 0.78 | 0.78 | 0.78 | 0.78 |
| Linoleic Acid | 0.10 | 0.10 | 0.10 | 0.10 | 0.10 | 0.10 | 0.10 | 0.10 |
| Stearic Acid | 0.25 | 0.25 | 0.25 | 0.25 | 0.25 | 0.25 | 0.25 | 0.25 |
| Cholesterol | 0.20 | 0.20 | 0.20 | 0.20 | 0.20 | 0.20 | 0.20 | 0.20 |
| Glycerin | 9.00 | 9.00 | 9.00 | 9.00 | 9.00 | 9.00 | 9.00 | 9.00 |
| Water | Qs | Qs | Qs | Qs | Qs | Qs | Qs | Qs |
| Sunscreens | | | | | | | | |
| UV Pearls ™ | — | 5.50 | — | — | — | — | — | — |
| SunCaps 664 ™ | — | — | 9.50 | — | — | — | — | — |
| Sylvaclear PA 1200V ® (1:1 with OMC) | — | — | — | 4.00 | — | — | — | — |
| Sylvaclear PA 1200V ® (4:6 with OMC) | — | — | — | — | 4.00 | — | — | — |
| Sylvaclear PA 1200V ® (6:4 with OMC) | — | — | — | — | — | 4.00 | — | — |
| Sylvaclear PA 1900V ® (1:1 with OMC) | — | — | — | — | — | — | 4.00 | — |
| Non-encapsulated OMC (Octylmethoxycinnamate) | 6.00 | — | — | — | — | 2.00 | — | 2.00 |
| Non-encapsulated Sylvaclear PA1200V ® | — | — | — | — | — | — | — | 4.00 |
| Oil Phase | | | | | | | | |
| DC 200 (Dimethicone) | 1.00 | 7.00 | 7.00 | 7.00 | 7.00 | 25.00 | 7.00 | 1.00 |
| DC5225C (Dimethicone Copolyol/Cyclomethicone) | 0.50 | 0.50 | 0.50 | 0.50 | 0.50 | 0.50 | 0.50 | 0.50 |
| DC9045 (Silicone Elastomer) | 20.00 | 20.00 | 20.00 | 20.00 | 20.00 | — | 20.00 | 20.00 |
| Polymers | | | | | | | | |
| Aristoflex AVC (Taurate Copolymer) | 0.80 | 0.80 | 0.80 | 0.80 | 0.40 | 0.40 | 0.80 | 0.80 |

TABLE I-continued

| | Formula (Weight %) | | | | | | | |
|---|---|---|---|---|---|---|---|---|
| Component | 1 | 2 | 3 | 4 | 5 | 6 | 7 | 8 |
| Particulates | | | | | | | | |
| Z-cote HP-1 (Zinc Oxide) Titanium Dioxide | 2.00 | 2.00 | 2.00 | 2.00 | 2.00 | 2.00 | 2.00 | 2.00 |
| Ganzpearl GMP-0820 (Polymethylmethacrylate) | 0.50 | 0.50 | 0.50 | 0.50 | 0.50 | 0.50 | 0.50 | 0.50 |
| Luminosity Powder | | | | | | | | |
| Satin Mica | 0.50 | 0.50 | 0.50 | 0.50 | 0.50 | 0.50 | 0.50 | 0.50 |
| Timiron MP 111 (Titanium Dioxide Coated Mica) | 1.00 | 1.00 | 1.00 | 1.00 | 1.00 | 1.00 | 1.00 | 1.00 |

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Formulas were applied and spread uniformly onto a plate to leave a film of 2 mg/cm². The film was left to dry for 30 minutes. Subsequently an SPF reading was taken on the dried film using three measurements on different parts of the coated quartz plate and recording an average value.

Results of the SPF testing and the dielectric constants for each of the composite particles within the formulas is recorded in Table II below.

TABLE II

| Formula | Formula Actives | SPF Value | Dielectric Constant |
|---|---|---|---|
| 1 | Non-encapsualted (6% external OMC) | 13 | — |
| 2 | UV Pearls ® (2% internal OMC) | 13 | — |
| 3 | SunCaps ® 664 (2% internal OMC) | 15 | — |
| 4 | Sylvaclear PA 1200V ® and OMC Composite 1:1 (2% internal OMC) | 18 | 8.59 |
| 5 | Sylvaclear PA 1200V ® and OMC Composite 4:6 (2.4% internal OMC) | 14 | 8.05 |
| 6 | Sylvaclear PA 1200V ® and OMC Composite 6:4 (1.6% internal OMC) | 18 | 8.96 |
| 7 | Sylvaclear AF 1900V ® and OMC Composite 1:1 (2% internal OMC) | 9 | 6.00 |
| 8 | Non-encapsulated Sylvaclear PA1200V ® (2% external OMC) | 8 | 10.20 |

The data of Table II demonstrate that as the dielectric constant of a composite increases, the SPF also increases. For instance, the composite of Formula 7 evidences the lowest dielectric constant, having a value of 6. Here the SPF is only 9. By increasing the dielectric constant of the composite to 8.05 as seen in Formula 5, the SPF substantially increases to 14. A further increase of dielectric constant as shown in Formula 4 and 6 to respectively 8.96 and 8.59 further improves the SPF to 18.

Photostability is also effected by dielectric constant. Table III provides data on UV stability of the composites.

TABLE III

| Formula | Formula Actives | Dielectric Constant | Photostability MPF/(MPF)$^{int}$ |
|---|---|---|---|
| 1 | Non-encapsulated (6% external OMC) | — | 5.48 |
| 4 | Sylvaclear PA 1200V ® Composite 1:1 (2% internal OMC) | 8.59 | 15.0 |
| 5 | Sylvaclear PA 1200V ® Composite 4:6 (2.4% internal OMC) | 8.05 | 12.3 |
| 6 | Sylvaclear PA 1200V ® Composite 6:4 (1.6% internal OMC) | 8.96 | 15.1 |
| 7 | Sylvaclear AF 1900V ® Composite 1:1 (2% internal OMC) | 6.00 | 8.8 |

Photostability in Table III is measured at an exposure time of 40 minutes. The value represents the monochromatic protection factor (MPF) initially divided by the value after 40 minutes. MPF is equivalent to the SPF value at a specific wavelength. For the present experiments the wavelength is the peak maximum at 320 to 310 nm. The 40 minutes time is equivalent to 10 hours of solar exposure.

The data of Table III reveal that photostability of a composite increases with increasing dielectric constant. For instance, Formula 7 with a dielectric constant of 6 had a photostability of only 8.8. By contrast, Formulas 4 and 6 with dielectric constants of 8.59 and 8.96 had photostability values of 1 5 and 15.1. Intermediate was Formula 5 with dielectric constant of 8.05 and a photostability of 12.3. There is a direct correlation between increased dielectric constant and improved photostability.

EXAMPLE 3

A further series of experiments were conducted to evaluate how different additives placed into the composite particles can manipulate dielectric constant and thereby effect the SPF value. Table IV illustrates the additive material effects. The composite material is essentially identical to Formula 4 of the previous Example.

TABLE IV

| Formula | Additive (3%) | Dielectric Constant | SPF |
|---|---|---|---|
| 4 | Control | 8.59 | 18 |
| 9 | Dipropylene Glycol | 9.03 | 21 |

TABLE IV-continued

| Formula | Additive (3%) | Dielectric Constant | SPF |
|---|---|---|---|
| 10 | Pentylene Glycol | 9.71 | 25 |
| 11 | Corapan ® TQ* | 7.38 | 12 |
| 12 | Oxynex ® ST** | 6.71 | 10 |

*Diethylhexyl 2,6-Naphthalate
**Diethylhexyl Syringal Malonate

Data in Table IV demonstrates that increases in dielectric constant caused by addition of an additive results in a concomitant increase in SPF.

EXAMPLE 4

Illustrative cosmetic formulas according to the present invention are provided in Table V.

TABLE V

| | Formula (Weight %) | | | |
|---|---|---|---|---|
| Component | 1 | 2 | 3 | 4 |
| Stearic Acid | 18 | 18 | 18 | 18 |
| Niacinamide | 1 | 1 | 1 | 1 |
| Potassium Hydroxide (85%) | 0.6 | 0.6 | 0.6 | 0.6 |
| Cetyl Alcohol | 0.5 | 0.5 | 0.5 | 0.5 |
| Silicone Oil (DC 200) | 0.5 | 0.5 | 0.5 | 0.5 |
| Isopropyl Myristate | 0.75 | 0.75 | 0.75 | 0.75 |
| Methyl Paraben | 0.15 | 0.15 | 0.15 | 0.15 |
| Propyl Paraben | 0.15 | 0.15 | 0.15 | 0.15 |
| Titanium Dioxide | 0.20 | 0.20 | 0.20 | 0.20 |
| Octylmethoxycinnamate (OMC) | — | — | 6.00 | 6.00 |
| Sylvaclear PA 1200V ® Avobenzene as 1:1 Composite | 4.00 | — | 4.00 | 4.00 |
| Sylvaclear PA 1200V ® and OMC as 1:1 Composite | 4.00 | 4.00 | — | 4.00 |
| Avobenzene* | — | 4.00 | — | — |
| Water | To 100 | To 100 | To 100 | To 100 |

*Generic name for 4,4'-t-butyl methoxydibenzoylmethane.

What is claimed is:

1. Composite particles comprising an organic sunscreen agent dispersed within a condensation polymerized resin, the composite particles having a number average particle size ranging from about 10 to about 2,000 nm, the condensation polymerized resin having carboxylic acid groups, and wherein the composite particles have a dielectric constant ranging from 6.5 to 18.

2. The composite particles according to claim 1 wherein the dielectric constant ranges from 7 to 15.

3. The composite particles according to claim 1 wherein the dielectric constant ranges from 8 to 12.

4. The composite particles according to claim 1 wherein the sunscreen agent is selected from the group consisting of 2-ethylhexyl-p-methoxycinnamate, 4,4'-t-butyl methoxydibenzoylmethane, 2-hydroxy-4-methoxybenzophenone and mixtures thereof.

5. The composite particles according to claim 1 wherein the condensation polymerized resin is formed at least partially of polyamides.

6. The composite particles according to claim 1 wherein the resin is a polyalkyleneoxypolyamide.

7. The composite particles according to claim 1 wherein the resin has an acid number ranging from 3 to 15.

8. The composite particles according to claim 1 wherein the resin has an acid number ranging from 5 to 14.

9. The composite particles according to claim 1 wherein the organic sunscreen agent and the resin are present in a relative weight ratio of 5:1 to 1:10.

10. The composite particles according to claim 1 wherein the organic sunscreen agent and the resin are present in a relative weight ratio of about 1:1 to about 1:3.

11. A cosmetic composition comprising the composite particles of claim 1 and formulated as an oil and water emulsion.

* * * * *